United States Patent
Takenaka et al.

(10) Patent No.: US 9,433,883 B2
(45) Date of Patent: Sep. 6, 2016

(54) DEVICE AND METHOD FOR COLLECTING AIRBORNE MICROORGANISMS

(75) Inventors: Kei Takenaka, Tokyo (JP); Yasuhiko Sasaki, Tokyo (JP); Shigenori Togashi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 559 days.

(21) Appl. No.: 13/985,708

(22) PCT Filed: Feb. 22, 2011

(86) PCT No.: PCT/JP2011/053850
§ 371 (c)(1),
(2), (4) Date: Aug. 15, 2013

(87) PCT Pub. No.: WO2012/114458
PCT Pub. Date: Aug. 30, 2012

(65) Prior Publication Data
US 2013/0319239 A1    Dec. 5, 2013

(51) Int. Cl.
*G01N 1/24* (2006.01)
*B01D 45/08* (2006.01)
*G01N 1/22* (2006.01)

(52) U.S. Cl.
CPC .............. *B01D 45/08* (2013.01); *G01N 1/2208* (2013.01); *G01N 1/2273* (2013.01); *G01N 2001/245* (2013.01)

(58) Field of Classification Search
CPC combination set(s) only.
See application file for complete search history.

(56) References Cited

U.S. PATENT DOCUMENTS

| | | | | |
|---|---|---|---|---|
| 6,240,768 B1 * | 6/2001 | Lemonnier | .......... | G01N 1/2273 73/28.05 |
| 6,472,203 B1 * | 10/2002 | Gallup | .......... | C12M 23/10 435/305.4 |
| 6,565,638 B1 * | 5/2003 | Sugita | .......... | G01N 1/2273 73/28.05 |
| 2008/0070292 A1 * | 3/2008 | Bridenne | .......... | G01N 1/2208 435/287.3 |
| 2011/0183371 A1 * | 7/2011 | Noda | .......... | C12Q 1/008 435/39 |

FOREIGN PATENT DOCUMENTS

| | | |
|---|---|---|
| JP | 2000-23662 A | 1/2000 |
| JP | 2000-300246 A | 10/2000 |
| JP | 2009-11265 A | 1/2009 |
| JP | 2009-55790 A | 3/2009 |
| JP | WO 2009157510 A1 * 12/2009 | ............. C12Q 1/008 |
| JP | 2010-124711 A | 6/2010 |
| WO | WO 99/37990 A1 | 7/1999 |
| WO | WO 2009/157510 A1 | 12/2009 |

OTHER PUBLICATIONS

J. Keskinen et al., "Electrical Low Pressure Impactor", J. Aerosol Sci. vol. 23, pp. 353-360 (1992).
International Search Report dated May 24, 2011 w/ partial English translation (five (5) pages).

* cited by examiner

*Primary Examiner* — Duane Smith
*Assistant Examiner* — Adam W Bergfelder
(74) *Attorney, Agent, or Firm* — Crowell & Moring LLP (57) ABSTRACT

The present invention provides an impaction-based microorganism collecting device in which microorganisms are captured by the capture surface of a collection plate. The microorganism collecting device is designed to reduce the influence of the lateral wind flowing over the perforated plate having multiple nozzles and also prevent warpage of the perforated plate.

Multiple air vents are formed around the circumference of the capture surface and through the capture surface so that air that has flowed through the nozzles of the perforated plate onto the capture surface can be discharged. This allows the air to flow in multiple directions over the capture surface, thereby reducing the speed of the air and increasing the microorganism capture rate.

14 Claims, 7 Drawing Sheets

DEVICE AND METHOD FOR COLLECTING AIRBORNE MICROORGANISMS

TECHNICAL FIELD

The present invention relates to a device and method for collecting airborne microorganisms and the like.

BACKGROUND ART

Devices for collecting airborne particles (airborne particle collectors) are now on the market. Among them are those that utilize impaction, and such airborne particle collectors have a high capture rate of microparticles and are now receiving attention.

Impaction refers to a method of impacting particle-containing air through nozzles onto a capture surface and thereby attaching the particles to the surface.

Conditions for collecting particles by impaction are expressed by the Stokes number $S_k$ given below.

$$S_k = pd^2 uC/9\mu w \quad (1)$$

where w is the diameter of the nozzles, u is the average air speed in the nozzles, $\mu$ is the viscosity coefficient of the air, p is the density of the particles, d is the diameter of the particles, and C is the Cunningham correction factor (the correction factor for particle movements, about 1.15 under atmospheric pressure).

According to "Aerosol Technology: the Critical Particle Diameter and the Collection Efficiency of Impactors," (Inoue Shoin, April 1985), when the square root of the Stokes number $S_k$ of the above formula (1) is 0.7 or higher, nearly 100% of the particles will collide with the capture surface.

Airborne microorganism collecting devices that utilize impaction can be classified into two types: those designed for collecting bacteria (minimum particle size=about 1 μm) and those designed for collecting aerosols (minimum particle size=several tens of micrometers).

Examples of the airborne microorganism collecting devices designed for collecting bacteria include the portable airborne bacteria sampler disclosed in Patent Document 1 and the air sampler and sampling method for microbiological analysis disclosed in Patent Document 2 (see below).

Those devices collect bacteria by impacting bacteria-containing air from multiple nozzles onto a culture medium (i.e., a capture surface). The air impacted onto the capture surface then flows through the space between the culture medium and the nozzle-including plate toward the circumferentially outer side of the capture surface.

An example of devices for collecting aerosols (minimum particle size=several tens of micrometers, which is much smaller than that of bacteria) is the low pressure impactor disclosed in Non-Patent Document 1. This impactor uses a vacuum pump to suction air. By the vacuum pump greatly lowering the exit-side pressure of the nozzles, the Cunningham correction factor C can be increased. As a result, the Stokes number of Formula (1) is also increased, allowing capture of very small particles.

The low pressure impactor of Patent Document 3 is designed such that when air is impacted from the nozzles onto the capture surface, the air flows toward the air vent located at the center of the capture surface.

PRIOR ART DOCUMENTS

Patent Documents

Patent Document 1: JP-2000-300246-A (U.S. Granted Pat. No. 6,565,638 B1)
Patent Document 2: JP-2000-23662-A
Patent Document 3: PCT WO99/37990

Non-Patent Document

Non-Patent Document 1: J. Keskinen, K. Pietarinen and M. Lehtimaki, "Electrical Low Pressure Impactor," J. Aerosol Sci., Vol. 23, pp 353-360, 1992

SUMMARY OF THE INVENTION

Problems to be Solved by the Invention

Among airborne microorganisms, there are organisms much smaller than bacteria such as viruses, and the number of microorganisms present in the atmosphere is very small. For these reasons, if such tiny microorganisms are to be collected, a copious amount of air needs to be suctioned.

Take influenza viruses, for example. According to T. P. Weber and N. I. Stilianakis ("Inactivation of Influenza A Viruses in the Environment and Modes of Transmission: a Critical Review," J Infect, Vol. 57, No. 5, pp 361-373, 1991), the diameters of the virus aggregates contained in the air exhaled from an influenza-infected patient are said to be in the range of 0.5 to 5 μm. Also, E. Cole and C. Cook state that the number of the virus aggregates contained in a sneeze of an infected patient is about 40,000 to 100,000 ("Characterization of Infectious Aerosols in Health Care Facilities: an Aid to Effective Engineering Controls and Preventing Strategies," Am J Infect Control, Vol. 26, No. 4, pp 453-464, 1998). When the volume of a particular space is assumed to be 100 $m^3$, the number of the virus aggregates present per 1 $m^3$ is 400 to 1,000, which is considerably low.

In the devices of Patent Documents 1 and 2, a copious amount of air can be suctioned because a fan is used for that purpose. However, those devices are designed to collect bacteria (minimum particle size=about 1 μm), and difficulty is involved in collecting much smaller microorganisms such as virus aggregates. In contrast, the device of Patent Document 3 is capable of collecting very tiny particles such as aerosols (minimum particle size=several tens of micrometers). However, since this device uses a vacuum pump for air suction, there is an upper limit to the amount of air suction, and a larger device volume is required.

In view of the above, collection of airborne microorganisms necessitates a device whose air suction amount is almost equal to those of bacteria collecting devices and that is capable of collecting very tiny microorganisms such as virus aggregates.

For that purpose, one possible method would be to reduce the diameter of the nozzles and increase the number of the nozzles. According to the above formula (1), reducing the diameter of the nozzles increases the Stokes number, allowing tiny particles to be collected. However, when the diameter of the nozzles becomes smaller, the amount of air passing through the nozzles also decreases. Thus, to maintain a sufficient amount of air suction at the same time, the number of the nozzles needs to be increased. However, the above method of reducing the diameter of the nozzles and at the same time increasing the number of the nozzles entails the following two issues.

One is a reduced capture rate. When the number of the nozzles increases, the intervals of the nozzles become smaller. This in turn increases the flow rate of the air flowing through the space between the perforated plate having the nozzles and the collection plate (such an air flow is hereinafter called "the lateral wind"), and the increased flow rate of the lateral wind reduces the capture rate.

The other is a larger warp of the perforated plate. When the diameter of the nozzles is reduced, pressure loss increases, which causes the perforated plate to warp more. Such a large warp will result in varied distances between the perforated plate and the collection plate, and the capture rate may vary depending on the locations of the nozzles.

One of the objects of the invention is therefore to provide an impaction-based airborne microorganism collecting device and method that prevents the lateral wind from reducing the capture rate and also prevents the capture rate from varying due to warpage of the perforated plate.

Means for Solving the Problem

To achieve the above object, the invention provides a microorganism collecting device comprising: a perforated plate having a plurality of nozzles that allow passage of air containing microorganisms; a collection plate facing the plurality of nozzles and having a capture surface for capturing the microorganisms; a collection plate holder for holding the collection plate; a fan for allowing the air to flow from the perforated plate toward the collection plate; a housing for holding the perforated plate, the collection plate holder, and the fan; and an air vent located in a space between the housing and circumferentially outer sections of the collection plate and the collection plate holder, wherein the device further has a second air vent formed at circumferentially inner sections of the collection plate and the collection plate holder.

The distance between the perforated plate and the collection plate is preferably ⅓ to 15 times the diameter of the nozzles.

It is also preferred that the perforated plate be a metal plate that is 0.01 to 2 mm in thickness and 5 to 200 mm in diameter, and that the nozzles of the perforated plate be 1,000 to 10,000 in number and each circular with the diameter of the nozzles being 50 to 200 µm.

The collection plate is preferably formed from a solid medium whose primary materials include glass, quartz, resin (polypropylene, polyethylene terephthalate, polycarbonate, polystyrene, acrylonitrile-butadiene-styrene resin, polymethacrylic acid methyl ester or other acrylic resin, polydimethylsiloxane), metal (pure metals such as iron, aluminum, copper, tin, gold, silver, and the like and alloys such as alloy steel, copper alloy, aluminum alloy, nickel alloy, and the like), gelatin, and agar.

Preferably, the collection plate includes concentric ring structures of different sizes whose top surfaces act as capture surfaces of the collection plate, and the spaces between the concentric ring structures act as air vents.

It is also preferred that ring-shaped convex portions be placed on the collection plate such that the convex portions are directly below the nozzles. The top surfaces of the convex portions act as capture surfaces of the collection plate, and the spaces between the convex portions communicate with the air vents.

It is further preferred that the areas of the top surfaces of the convex portions be each about 1 to 4 times the area of each of the nozzles, and that the height of the convex portions be about 1 to 5 times the diameter of each of the convex portions.

It is still further preferred that one or more support columns be formed on the collection plate to support the perforated plate.

To achieve the above object, the invention also provides a method for collecting airborne microorganisms, the method comprising the steps of: causing the air to flow through the nozzles of the perforated plate toward the capture surface(s) of the collection plate; causing the capture surface(s) to capture the microorganisms contained in the air; and causing the air to flow toward both the air vent and the second air vent after flowing past the nozzles.

Effect of the Invention

The invention provides an airborne microorganism collecting device and method that prevent the lateral wind from reducing the capture rate and also prevent the capture rate from varying due to warpage of the perforated plate.

MODE FOR CARRYING OUT THE INVENTION

The spread of viruses such as avian influenza viruses and foot-and-mouth disease viruses is now a social issue, requiring urgent measures to prevent it. Thus, it is an urgent task to collect a great number of viruses and identify their causes.

One possible method would be collection of viruses using the impaction method mentioned earlier. The impaction method, however, is designed for collection of bacteria and not suited for collection of viruses, which are smaller in particle diameter than bacteria. For this reason, we attempted to increase the rate of virus capture by reducing the diameter of the nozzles that allow passage of air for the small particle diameters of viruses. However, it turned out that a small nozzle diameter would limit the amount of air passing through the nozzles.

Thus, we also considered increasing the amount of air supply by increasing the number of nozzles in the plate. However, due to the location of the air vent, the air discharged from the nozzles was caused to flow laterally toward the air vent (such an air flow is hereinafter called "the lateral wind"), which resulted in a reduced virus capture rate. Moreover, the increase in the number of nozzles also caused the perforated plate to warp, resulting in varied virus capture rates.

Therefore, we gave various considerations to what structure could reduce the speed of the lateral wind and prevent warpage of the perforated plate, the results of which will be described in the embodiments that follow.

First, it is to be noted that the term "microorganism collecting device or method" as used herein refers to a device or method used to examine viruses, bacteria, yeasts, protozoa, fungi, spores, and pollen. Note also that for simplification purposes, the term "microorganisms" as used herein is meant to include not only common microorganisms (e.g., bacteria, yeasts, protozoa, and fungi), but also viruses, spores, and pollen.

We now describe embodiments of the invention with reference to the accompanying drawings. The embodiments described below are only meant to be examples, meaning that all the embodiments can be combined with one another and that some aspects of the embodiments can be combined with or replaced by known techniques.

Embodiment 1

Figure 1:
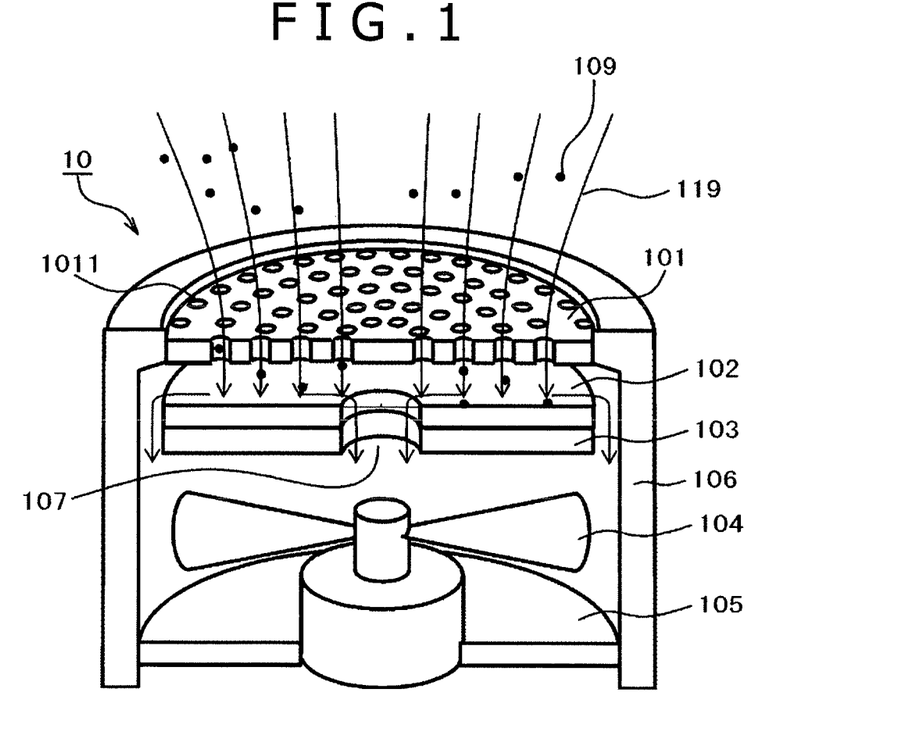
FIG. 1 schematically illustrates the structure of a microorganism collecting device according to Embodiment 1 of the invention.

(A) Method of Increasing the Capture Rate by Reducing the Influence of the Lateral Wind FIG. 1 schematically illustrates the structure of a microorganism colleting device according to an embodiment of the invention.

The microorganism collecting device 10 of FIG. 1 includes the following components: a perforated plate 101 having multiple nozzles 1011; a collection plate 102 having a microorganism capture surface; a collection plate holder 103 for holding the collection plate 102; a fan 104 for suctioning air; a filter 105 for filtering the suctioned air; and a housing 106 for holding the perforated plate 101, the collection plate holder 103, the fan 104, and the filter 105.

The collection plate 102 and the collection plate holder 103 are both doughnut-shaped, and an inner vent 107 and an outer vent 108 are disposed on the circumferentially inner and outer sides of those components for allowing passage of suctioned air. Although not illustrated in FIG. 1, the housing 106 and the collection plate holder 103 are connected to each other by beam-like structures.

As above, by shaping the collection plate 102 and the collection plate holder 103 into doughnut-like structures, the microorganism collecting device 10 of Embodiment 1 includes not only the outer vent 108, but also the inner vent 107, which acts as the second vent. As illustrated in FIG. 1, the inner vent 107 is placed at substantially the same position as the rotary shaft of the fan 104.

Collection of airborne virus aggregates 109 by the microorganism collecting device 10 is performed in the following manner.

When the fan 104 starts to rotate, air flows 119 are generated, causing air to flow into the nozzles 1011 of the perforated plate 101. Transported by the air flows 119, the virus aggregates 109 contained in the air also flow into the nozzles 1011. Once inside the device 10, the air collides with the capture surface of the collection plate 102 and then flows over the surface. When the inertia forces of the virus aggregates 109 are large relative to the power of the air flows 109, the virus aggregates 109 will not be transported by the air flows, but will collide with the surface of the collection plate 102 and be captured.

As the Stokes number given in the aforementioned formula (1) becomes large, the chances of the virus aggregates 109 colliding with the collection plate 102 increase accordingly.

Part of the drawn air is then directed toward the inner vent 107 while the rest is directed to the outer vent 108, and eventually the air inside the device 10 is discharged out of the device 10 through the filter 105. Virus aggregates 109 that have escaped capture are filtered when they pass through the filter 105. After virus capture has been completed, the collection plate 102 is removed from the device 10 and then rinsed in water or a buffer solution. Doing so allows the virus aggregates 109 captured onto the collection plate 102 to be extracted into the solution.

The extracted viruses will be detected with the use of virus culturing cells. When a gene detection method is to be employed for virus detection, the collection plate 102 that has captured virus aggregates 109 will be rinsed in a gene eluting reagent made mainly from a guanidinium salt to elute the genes of the viruses. Thereafter, the virus genes eluted into the reagent can be extracted by solid-phase extraction, followed by the detection of the virus genes based on a PCR method or other gene detection method.

The following is an advantage of the multiple vents.

After air passes through the nozzles 1011 and reaches the collection plate 102, the air will change greatly in terms of its flow direction and flow through the space between the perforated plate 101 and the collection plate 102 (this air flow is called the lateral wind). If the nozzles 1011 become larger in number and smaller in nozzle-to-nozzle interval, the influence of the lateral wind increases, causing the air to flow obliquely from the nozzles 1011 up to the collection plate 102. As the air flows more obliquely, changes of air directions over the collection plate 102 become smaller, which would result in a reduced capture rate of virus aggregates 109. Because the speed of the lateral wind is higher on the downstream side, the capture rate of virus aggregates 109 passing through downstream nozzles 1011 is smaller than the capture rate of virus aggregates 109 passing through upstream nozzles 1011.

If a single air vent is disposed on the circumferentially outer or inner side of the collection plate 102, the lateral wind flows from the inner side to the outer side or vice versa. Thus, the inner vent 107 and the outer vent 108 are provided to make the lateral wind flow toward both the inner side and the outer side, thereby reducing the speed of the lateral wind.

Some of the components are now discussed. The perforated plate 101 is a metal plate that is 0.01 to 2 mm in thickness and 5 to 200 mm in diameter. The diameter of the nozzles 1011 of the perforated plate 101 is determined by the diameters of particles to be captured, and the number of the nozzles 1011 is determined by the diameter of the nozzles 1011 and by the amount of air intake. According to the aforementioned formula (1), if more than 90% of 300 μm particles are to be collected at an air intake rate of 0.1 m$^3$/min, the diameter of the nozzles 1011 needs to be 200 μm or less and preferably in the range of 50 to 100 μm in light of nozzle machinability and the turbulence of air passing through the nozzles.

In that case, the number of nozzles that meets the above air intake rate is 1,000 to 10,000. As to the pitch of the nozzles, the larger the pitch, the lower the speed of the lateral wind. However, a larger pitch requires the perforated plate 101 to be increased in size. In light of this trade-off, it is therefore preferred that the pitch of the nozzles 1011 be 0.5 to 2 mm. The nozzles can be formed by etching, laser machining, electro-spark machining, electron beam machining, or mechanical machining.

The collection plate 102 is a flat plate and preferably formed from a solid medium whose primary materials include glass, quartz, resin (polypropylene, polyethylene terephthalate, polycarbonate, polystyrene, acrylonitrile-butadiene-styrene resin, polymethacrylic acid methyl ester or other acrylic resin, polydimethylsiloxane), metal (pure metals such as iron, aluminum, copper, tin, gold, silver, and the like and alloys such as alloy steel, copper alloy, aluminum alloy, nickel alloy, and the like), gelatin, and agar.

The optimal distance between the perforated plate 101 and the collection plate 102 depends on the diameter of the nozzles 1011, but it is preferably ⅓ to 15 times the nozzle diameter and more preferably ½ to 5 times the nozzle diameter.

The filter 105 is a HEPA (high efficiency particulate air) filter and used to remove uncollected virus aggregates.

Figure 2:
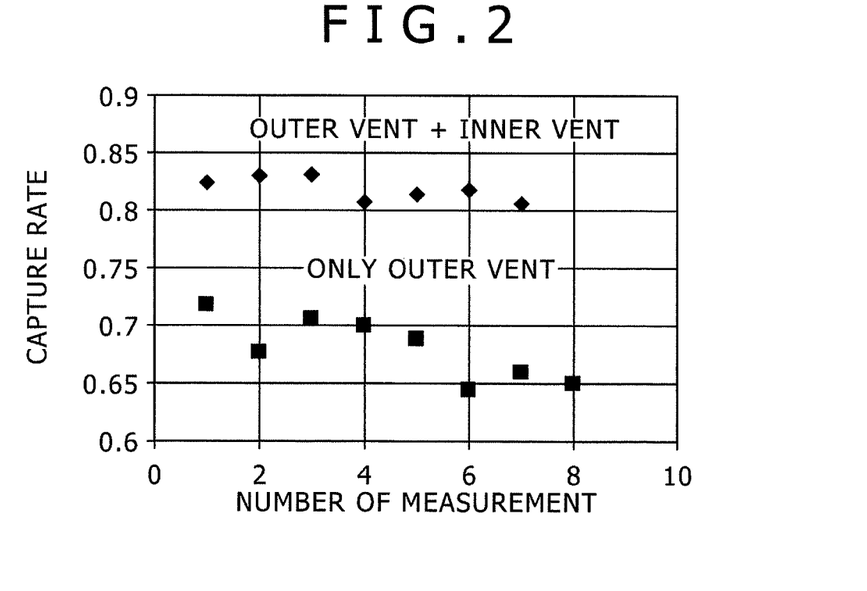
FIG. 2 is a graph showing the virus capture rate of the microorganism collecting device of Embodiment 1.

FIG. 2 is a graph showing the virus capture rate of the microorganism collecting device of Embodiment 1.

In FIG. 2, 0.3 μm pseudo-viruses (polystyrene particles) were dispersed in a space and collected by using microorganism collecting devices 10. One is the microorganism collecting device 10 of Embodiment 1, and the other is another microorganism collecting device 10 without the inner vent 107. Each of the devices was subjected to the capture rate measurement eight times.

The capture rate 1 was calculated from the following equation (2).

Capture rate 1=(the number of particles contained in the air before the air's passage through the perforated plate 101–the number of particles contained in the air that has passed through the vent(s))/the number of particles contained in the air before the air's passage through the perforated plate 101   (2)

In FIG. 2, the squares represent the capture rate of the microorganism collecting device 10 without the inner vent 107 while the rhombuses represent the capture rate of the microorganism collecting device 10 of Embodiment 1 (with the inner vent 107 and the outer vent 108). As illustrated, the microorganism collecting device 10 of Embodiment 1 recorded higher capture rates.

Embodiment 2

Figure 3:
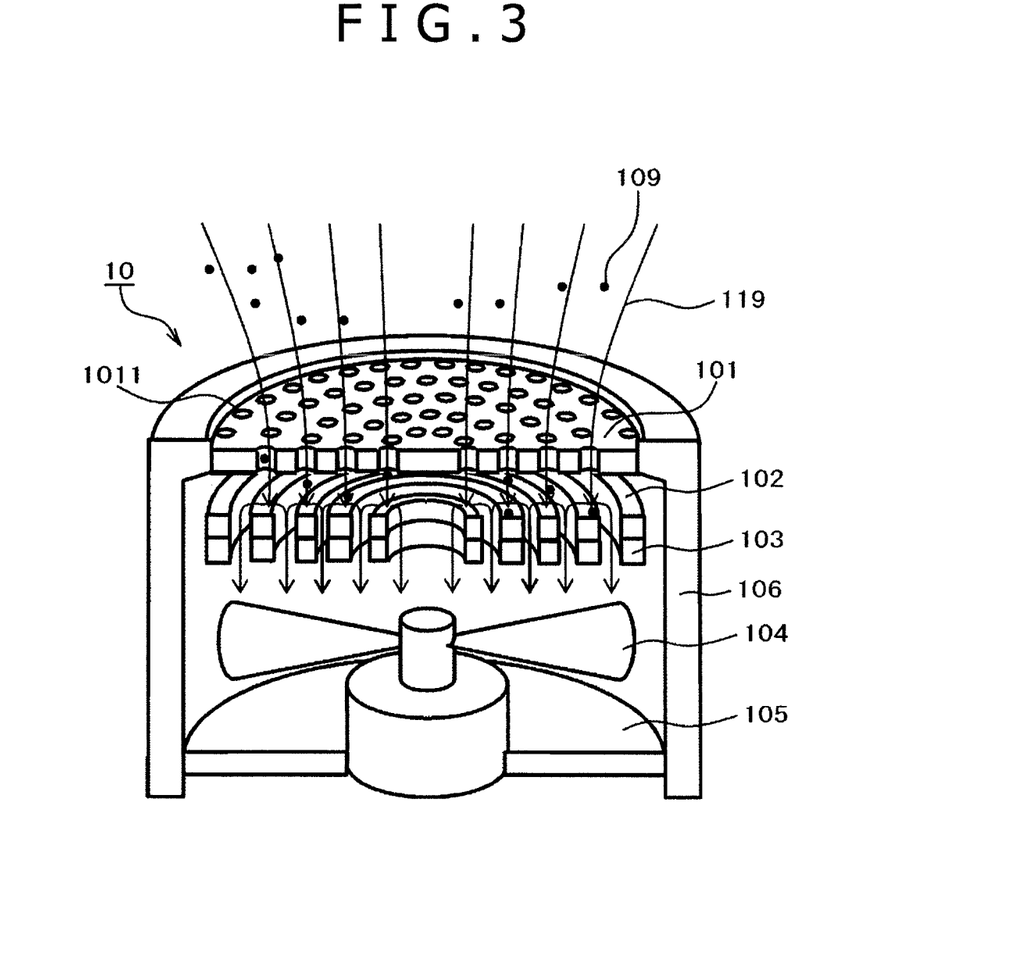
FIG. 3 schematically illustrates the structure of a microorganism collecting device according to Embodiment 2 of the invention.

FIG. 3 schematically illustrates the structure of a microorganism collecting device according to Embodiment 2 of the invention.

As illustrated in FIG. 3, the microorganism collecting device 10 of Embodiment 2 has more air vents than in FIG. 1 and is thus less subject to the influence of the lateral wind. Specifically, the collection plate 102 and the collection plate holder 103 are provided with multiple ring-shaped holes such that the holes are not located directly below the nozzles 1011 of the perforated plate 101. The collection plate 102 and the collection plate holder 103 are shaped like concentric rings of various sizes. Although not illustrated, the ring structures of the collection plate 102 or of the collection plate holder 103 are connected to one another by beam-like structures to keep them in place. When air passes through the nozzles 1011 and reaches the collection plate 102, the collection plate 102 changes the direction of the air, causing the air to flow into the holes. Because the microorganism collecting device of Embodiment 2 lowers the speed of the lateral wind flowing over the collection plate 102, the virus capture rate can be increased.

When there is no influence of the lateral wind, a virus aggregate 109 flowing past one of the nozzles will collide with the surface of the collection plate 102 that is directly below that nozzle. The collision area will become larger as the speed of the air flowing through the nozzle becomes lower. To allow for some expansion of collision areas and displacement of the collection plate 102 relative to the nozzles 1011, the width of the ring structures of the collection plate 102 is preferably 1 to 2 times the diameter of the nozzles 1011.

Embodiment 3

Figure 4:
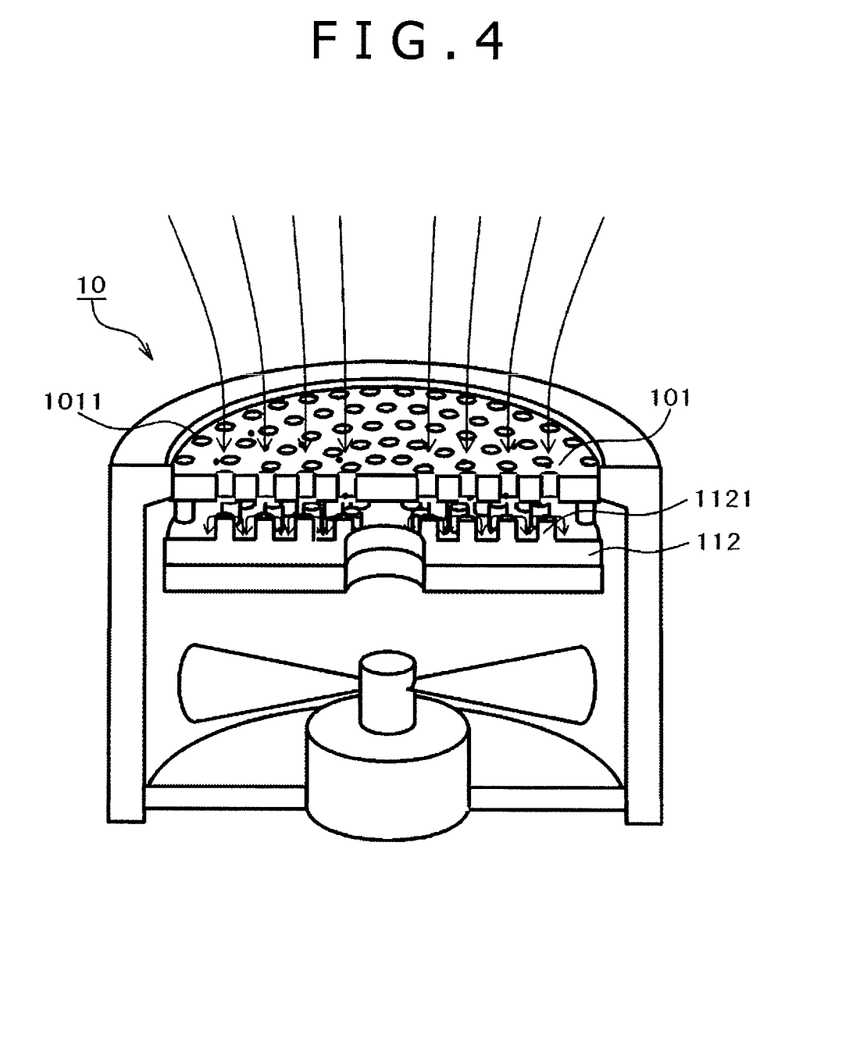
FIG. 4 schematically illustrates the structure of a microorganism collecting device according to Embodiment 3 of the invention.

FIG. 4 schematically illustrates the structure of a microorganism collecting device according to Embodiment 3 of the invention.

As illustrated in FIG. 4, the microorganism collecting device 10 of Embodiment 3 includes an irregular collection plate 112 having irregularity to reduce the influence of the lateral wind.

Since reducing the influence of the lateral wind is important for increasing the particle capture rate, convex portions 1121 are disposed directly below the nozzles 1011 of the perforated plate 101. When air passes through the nozzles 1011 and reaches the irregular collection plate 112, the convex portions 112 change the direction of the air, causing the air to flow down to the concave portions of the irregular collection plate 112. This allows reducing the amount of air flowing over the top surfaces of the convex portions 1121, resulting in less influence of the lateral wind and an increased capture rate.

When there is no influence of the lateral wind, a virus aggregate 109 flowing past one of the nozzles 1011 will collide with the surface of the irregular collection plate 112 that is directly below that nozzle. The collision area will become larger as the speed of the air flowing through the nozzle becomes lower. To allow for some expansion of collision areas and displacement of the convex portions 1121 relative to the nozzles 1011, the area of the convex portions 1121 is preferably 1 to 4 times the area of the nozzles 1011. It is also preferred that the height of the convex portions 1121 be 1 to 5 times the diameter of the convex portions 1121. This is preferred in terms of the machinability and structural strength of the convex portions 1121 although a larger height of the convex portions 1121 makes the influence of the lateral wind smaller.

(B) Method of Preventing Warpage of the Perforated Plate Using a Support Column

Embodiment 4

Figure 5:
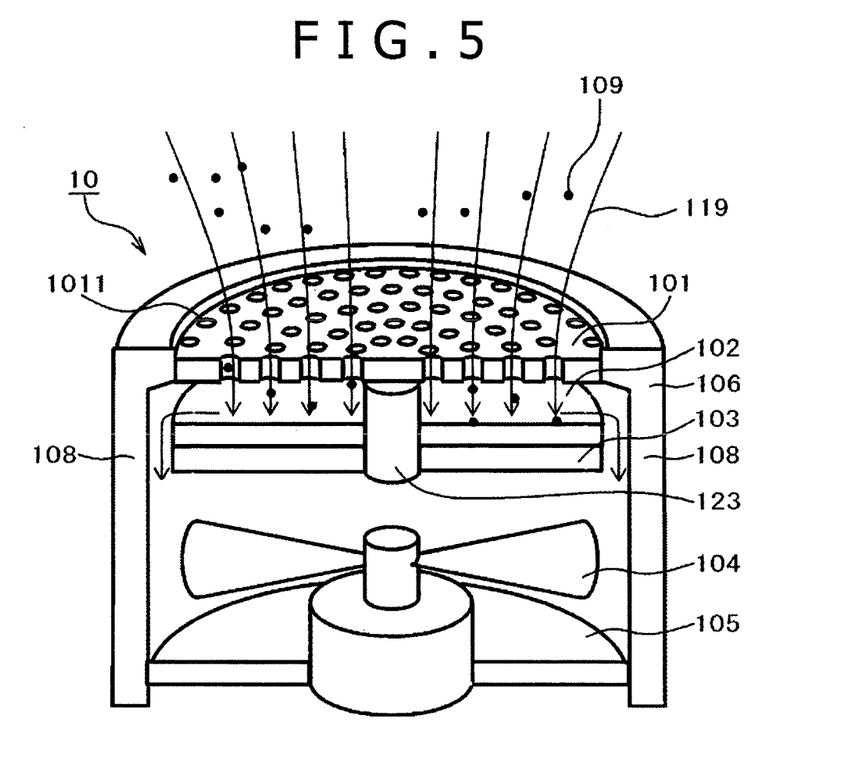
FIG. 5 schematically illustrates the structure of a microorganism collecting device according to Embodiment 4 of the invention.

FIG. 5 schematically illustrates the structure of a microorganism collecting device according to Embodiment 4 of the invention.

The microorganism collecting device 10 of FIG. 5 includes the following components: a perforated plate 101 having multiple nozzles 1011; a collection plate 102 having a microorganism capture surface; a collection plate holder 103 for holding the collection plate 102; a fan 104 for suctioning air; a filter 105 for filtering the suctioned air; and a housing 106 for holding the perforated plate 101, the collection plate holder 103, the fan 104, and the filter 105. The collection plate holder 103 of this embodiment is circular and includes a support column 123 for supporting the perforated plate 101.

Collection of airborne virus aggregates 109 by the microorganism collecting device 10 is performed in the following manner. When the fan 104 starts to rotate, air flows 119 are generated, causing air to flow into the nozzles 1011 of the perforated plate 101. Transported by the air flows 119, the virus aggregates 109 contained in the air also flow into the nozzles 1011. Once inside the device 10, the air collides with the capture surface of the collection plate 102 and then flows over the surface. When the inertia forces of the virus aggregates 109 are large relative to the power of the air flows 109, the virus aggregates 109 will not be transported by the air flows 119, but will collide with the surface of the collection plate 102 and be captured.

As the Stokes number given in the aforementioned formula (1) becomes large, the chances of the virus aggregates 109 colliding with the collection plate 102 increase accordingly. Part of the drawn air is then directed toward the inner vent 107 while the rest is directed to the outer vent 108, and eventually the air inside the device 10 is discharged out of the device 10 through the filter 105. Virus aggregates 109 that have escaped capture are filtered when they pass through the filter 105. After virus capture has been completed, the collection plate 102 is removed from the device 10 and then rinsed in water or a buffer solution. Doing so allows the virus aggregates 109 captured onto the collection plate 102 to be extracted into the water or buffer solution.

The extracted viruses will be detected with the use of virus culturing cells. When a gene detection method is to be employed for virus detection, the collection plate 102 that has captured virus aggregates 109 will be rinsed in a gene eluting reagent made mainly from a guanidinium salt to elute the genes of the viruses. Thereafter, the virus genes eluted into the reagent can be extracted by solid-phase extraction, followed by the detection of the virus genes based on a PCR method or other gene detection method.

During the capture of the virus aggregates 109, pressure loss causes pressure differences between the entrances and the exits of the nozzles 1011, which may in turn cause the perforated plate 101 to warp. Too large a warp will result in varied distances between the perforated plate 101 and the collection plate 102, and the capture rate may vary depending on the locations of the nozzles. Therefore, the support column 123 is provided to support the center of the perforated plate 101, so that such warpage can be minimized.

Figure 6:
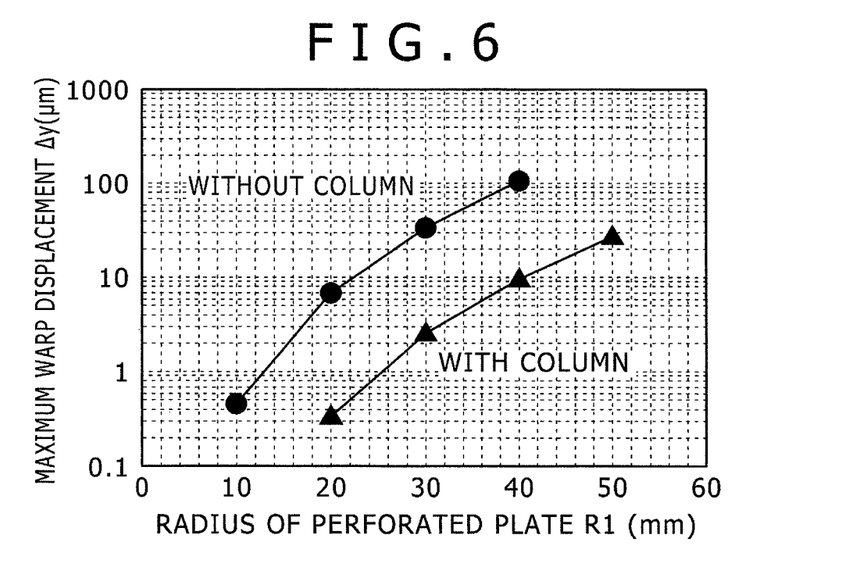
FIG. 6 is a graph showing the warp size of a perforated plate according to Embodiment 4.

FIG. 6 is a graph showing the warp sizes of the perforated plate 101 when supported and when not supported by the support column 123. While varying the radius of the perforated plate 101, we calculated the displacement of the perforated plate 101 by placing an equal load of 6 kPa across the perforated plate 101, and the largest displacement across the perforated plate 101 was plotted as the maximum warp displacement. In FIG. 6, the circles represent the warp displacement of the perforated plate 101 when not supported by the support column 123 while the triangles represent the warp displacement of the perforated plate 101 when supported by the support column 123. As illustrated, the latter warp displacement was about one tenth of the former warp displacement.

Embodiment 5

Figure 7:
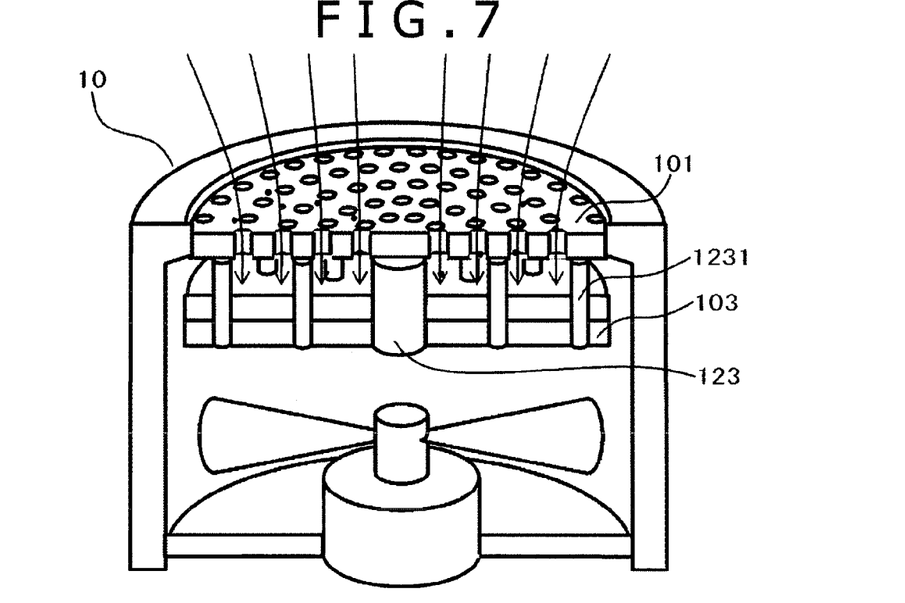
FIG. 7 schematically illustrates the structure of a microorganism collecting device according to Embodiment 5 of the invention.

FIG. 7 schematically illustrates the structure of a microorganism collecting device according to Embodiment 5 of the invention.

As illustrated in FIG. 7, to further reduce the warpage of the perforated plate, the microorganism collecting device 10 of Embodiment 5 further includes multiple support columns 1231, which are fixed to the collection plate holder 103. Since the perforated plate 101 is supported further by the support columns 1231, the warp of the perforated plate 101 of FIG. 7 becomes smaller than in FIG. 5.

(C) Method of Preventing Warpage of the Perforated Plate While Reducing the Influence of the Lateral Wind Embodiment 6

Embodiment 6 has the two advantages described in the aforementioned methods (A) and (B).

Figure 8:
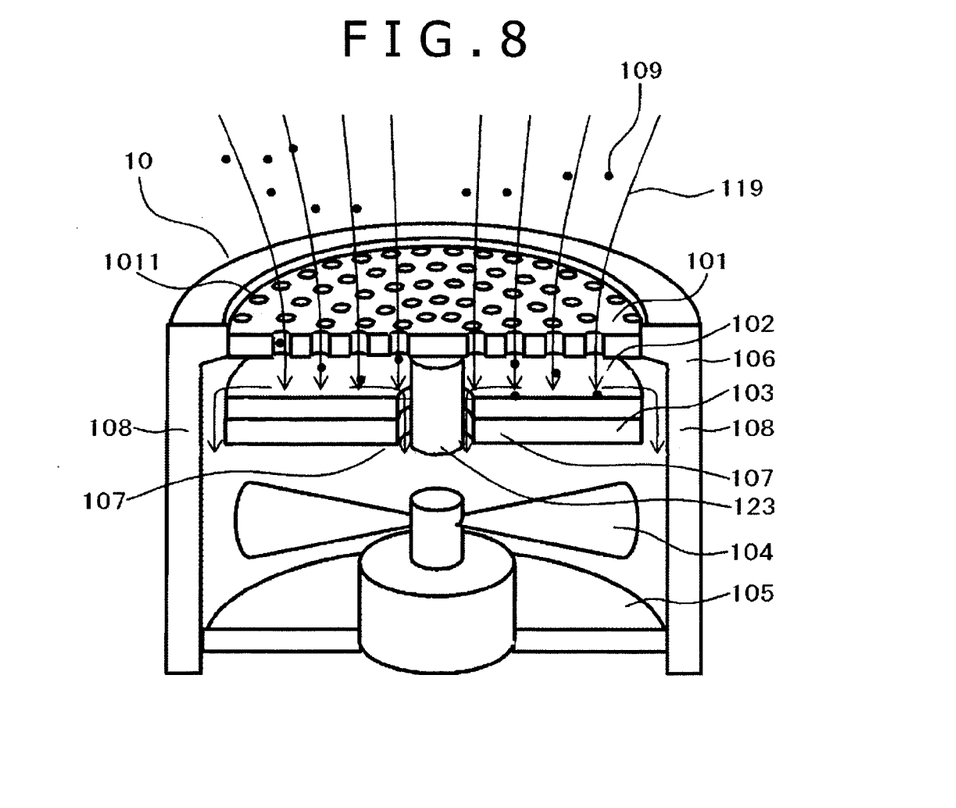
FIG. 8 schematically illustrates the structure of a microorganism collecting device according to Embodiment 6 of the invention.

FIG. 8 schematically illustrates the structure of a microorganism collecting device 10 according to Embodiment 6 of the invention.

The microorganism collecting device 10 of FIG. 8 includes the following components: a perforated plate 101 having multiple nozzles 1011; a collection plate 102 having a microorganism capture surface; a collection plate holder 103 for holding the collection plate 102; a fan 104 for suctioning air; a filter 105 for filtering the suctioned air; and a housing 106 for holding the perforated plate 101, the collection plate holder 103, the fan 104, and the filter 105.

The collection plate 102 and the collection plate holder 103 are both doughnut-shaped, and an inner vent 107 and an outer vent 108 are disposed on the circumferentially inner and outer sides of those components for allowing passage of suctioned air. The collection plate holder 103 includes a support column 123 for supporting the perforated plate 101.

Collection of airborne virus aggregates 109 by the microorganism collecting device 10 is performed in the following manner. When the fan 104 starts to rotate, air flows 119 are generated, causing air to flow into the nozzles 1011 of the perforated plate 101. Transported by the air flows 119, the virus aggregates 109 contained in the air also flow into the nozzles 1011. Once inside the device 10, the air collides with the capture surface of the collection plate 102 and then flows over the surface. When the inertia forces of the virus aggregates 109 are large relative to the power of the air flows 109, the virus aggregates 109 will not be transported by the air flows 119, but will collide with the surface of the collection plate 102 and be captured.

As the Stokes number given in the aforementioned formula (1) becomes large, the chances of the virus aggregates 109 colliding with the collection plate 102 increase accordingly. Part of the drawn air is then directed toward the inner vent 107 while the rest is directed to the outer vent 108, and eventually the air inside the device 10 is discharged out of the device 10 through the filter 105. Virus aggregates 109 that have escaped capture are filtered when they pass through the filter 105. After virus capture has been completed, the collection plate 102 is removed from the device 10 and then rinsed in water or a buffer solution. Doing so allows the virus aggregates 109 captured onto the collection plate 102 to be extracted into the water or buffer solution.

The extracted viruses will be detected with the use of virus culturing cells. When a gene detection method is to be employed for virus detection, the collection plate 102 that has captured virus aggregates 109 will be rinsed in a gene eluting reagent made mainly from a guanidinium salt to elute the genes of the viruses. Thereafter, the virus genes eluted into the reagent can be extracted by solid-phase extraction, followed by the detection of the virus genes based on a PCR method or other gene detection method.

In order to lower the speed of the air (lateral wind) flowing between the perforated plate 101 and the collection plate 102, the inner vent 107 and the outer vent 108 are provided so that the lateral wind flows toward both the inner side and the outer side.

During the capture of the virus aggregates 109, pressure loss causes pressure differences between the entrances and the exits of the nozzles 1011, which may in turn cause the perforated plate 101 to warp. Too large a warp will result in varied distances between the perforated plate 101 and the collection plate 102, and the capture rate may vary depending on the locations of the nozzles. Therefore, the support column 123 is provided to minimize such warpage.

Embodiment 7

Figure 9:
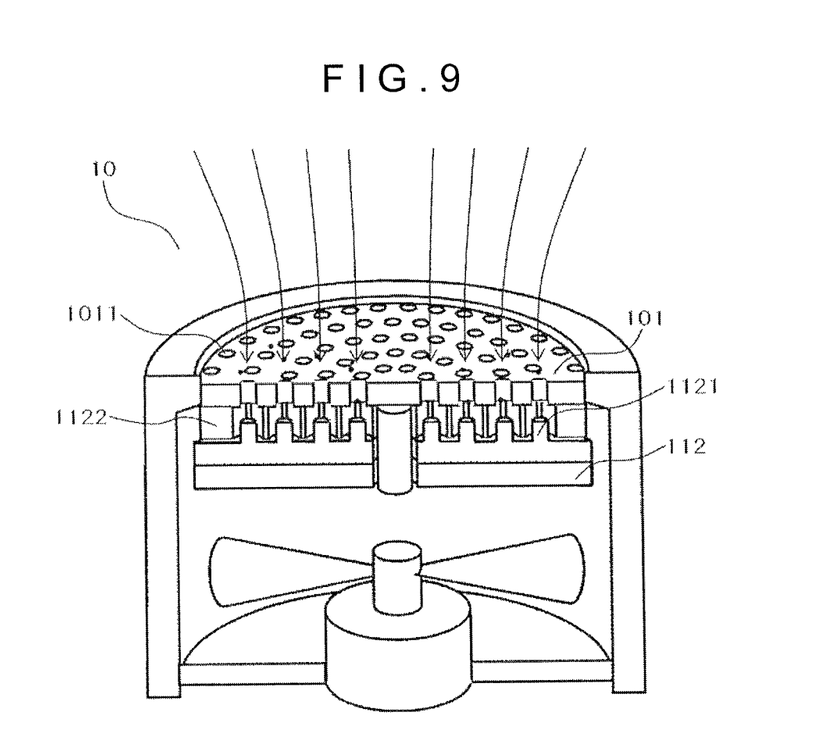
FIG. 9 schematically illustrates the structure of a microorganism collecting device according to Embodiment 7 of the invention.
Figure 10:
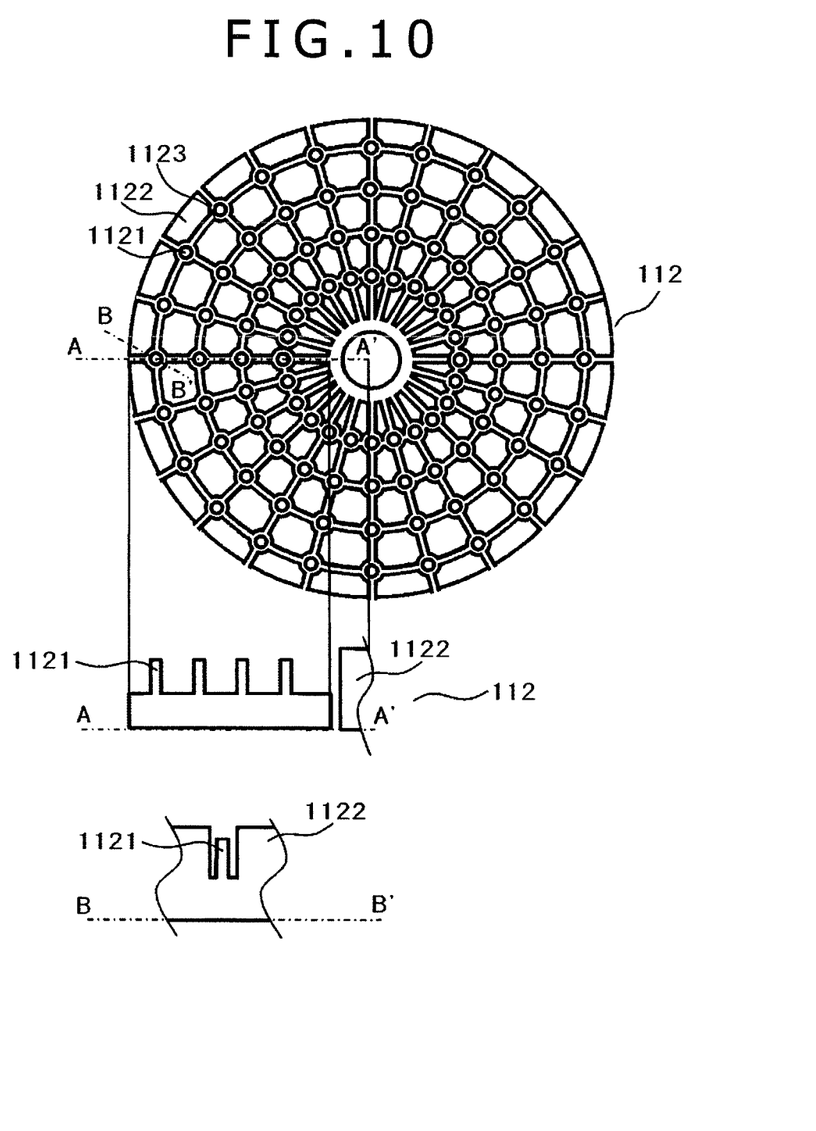
FIG. 10 illustrates the form of a collection plate according to Embodiment 7.

Embodiment 7 allows reducing the influence of the lateral wind as well as preventing warpage of the perforated plate 101 by changing the structure of the irregular collection plate 112.

FIG. 9 schematically illustrates the structure of a microorganism collecting device according to Embodiment 7 of the invention.

FIG. 10 illustrates the form of the irregular collection plate of Embodiment 7.

As illustrated in FIGS. 9 and 10, the irregular collection plate 112 has convex portions 1121 formed directly below the nozzles 1011 of the perforated plate 101. The irregular collection plate 112 also includes a continuous groove 1123 surrounding all the convex portions 1121 to guide air. The groove 1123 spreads from the inner side of the irregular collection plate 112 up to its outer side.

As illustrated in FIG. 10, the groove 1123 is shaped like a spider web, and the convex portions 1121 are placed at the intersections of the groove 1123. The portions of the irregular collection plate 112 other than the convex portions 1121 and the groove 1123 (i.e., wall portions 1122) are larger in height than the convex portions 1121. While the microorganism collecting device 10 is in use, the perforated plate 101 is pressed against the irregular collection plate 112, and the wall portions 1122 act as inter-nozzle compartment walls and also as a spacer between the convex portions 1121 and the nozzles 1011.

After air passes through the nozzles 1011 of the perforated plate 101 and reaches the irregular collection plate 112, the direction of the air is changed by the convex portions 1121, and the air then flows through the groove 1123 and eventually out of the device 10. As stated above, the height difference between the wall portions 1122 and the convex portions 1121 is secured as a space between the perforated plate 101 and the convex portions 1121, and the nozzles 1011 are surrounded by the wall portions 1122. As a result, the amount of air flowing over the convex portions 1121 can be reduced, which in turn reduces the influence of the lateral wind and increases the capture rate. In addition, since the greater part of the perforated plate 101 is supported by the wall portions 1122, warpage of the perforated plate 101 can be minimized, thus preventing the capture rate from varying depending on the locations of the nozzles 1011.

In summary, according to the present invention, multiple air vents are provided such that the air drawn through the nozzles of the perforated plate onto the capture surface is discharged through the air vents. This allows the lateral wind to flow in multiple directions over the capture surface, preventing the lateral wind from reducing the capture rate.

Furthermore, the collection plate having the capture surface includes one or more support columns for supporting the perforated plate, so that warpage of the perforated plate is prevented.

DESCRIPTION OF REFERENCE NUMERALS

10: Microorganism collecting device
101: Perforated plate
102: Collection plate
103: Collection plate holder
104: Fan
105: Filter
106: Housing
107: Inner vent
108: Outer vent
109: Virus aggregate
112: Irregular collection plate
123: Support column

The invention claimed is:

1. A microorganism collecting device comprising:
a perforated plate having a plurality of nozzles that allow passage of air containing microorganisms;
a collection plate facing the plurality of nozzles and having a capture surface for capturing the microorganisms;
a collection plate holder for holding the collection plate;
a fan for allowing the air to flow from the perforated plate toward the collection plate;
a housing for holding the perforated plate, the collection plate holder, and the fan; and
an air vent located in a space between the housing and circumferentially outer sections of the collection plate and the collection plate holder,
wherein the device further has a second air vent formed at circumferentially inner sections of the collection plate and the collection plate holder,
wherein ring-shaped convex portions are placed on the collection plate such that the convex portions are directly below the nozzles,
wherein the top surfaces of the convex portions act as capture surfaces of the collection plate, and
wherein the spaces between the convex portions communicate with the air vents.

2. The microorganism collecting device of claim 1 wherein the distance between the perforated plate and the collection plate is ⅓ to 15 times the diameter of the nozzles.

3. The microorganism collecting device of claim 1 wherein the perforated plate is a metal plate that is 0.01 to 2 mm in thickness and 5 to 200 mm in diameter, and wherein the nozzles of the perforated plate are 1,000 to 10,000 in number and each circular with the diameter of the nozzles being 50 to 200 µm.

4. The microorganism collecting device of claim 2 wherein the collection plate is formed from a solid medium selected from the group consisting of glass, quartz, resin (polypropylene, polyethylene terephthalate, polycarbonate, polystyrene, acrylonitrile-butadiene-styrene resin, polymethacrylic acid methyl ester or other acrylic resin, polydimethylsiloxane), metal (iron, aluminum, copper, tin, gold, silver, alloy steel, copper alloy, aluminum alloy, nickel alloy gelatin, and agar.

5. The microorganism collecting device of claim 1 wherein the collection plate includes concentric ring structures of different sizes whose top surfaces act as capture surfaces of the collection plate, and wherein the spaces between the concentric ring structures act as air vents.

6. The microorganism collecting device of claim 1 wherein the areas of the top surfaces of the convex portions are each about 1 to 4 times the area of each of the nozzles, and wherein the height of the convex portions is about 1 to 5 times the diameter of each of the convex portions.

7. The microorganism collecting device of claim 1 wherein one or more support columns are formed on the collection plate to support the perforated plate.

8. A method for collecting airborne microorganisms that involves the use of the microorganism collecting device of claim 1, the method comprising the steps of:
  causing the air to flow through the nozzles of the perforated plate toward the capture surface(s) of the collection plate;
  causing the capture surface(s) to capture the microorganisms contained in the air; and
  causing the air to flow toward both the air vent and the second air vent after flowing past the nozzles.

9. A microorganism collecting device comprising:
  a perforated plate having a plurality of nozzles that allow passage of air containing microorganisms;
  a collection plate facing the plurality of nozzles and having a capture surface for capturing the microorganisms;
  a collection plate holder for holding the collection plate;
  a fan for allowing the air to flow from the perforated plate toward the collection plate;
  a housing for holding the perforated plate, the collection plate holder, and the fan; and
  an air vent located in a space between the housing and circumferentially outer sections of the collection plate and the collection plate holder,
  wherein the device further has a second air vent formed at circumferentially inner sections of the collection plate and the collection plate holder,
  and wherein one or more support columns are formed on the collection plate to support the perforated plate.

10. The microorganism collecting device of claim 9 wherein the distance between the perforated plate and the collection plate is ⅓ to 15 times the diameter of the nozzles.

11. The microorganism collecting device of claim 9 wherein the perforated plate is a metal plate that is 0.01 to 2 mm in thickness and 5 to 200 mm in diameter, and wherein the nozzles of the perforated plate are 1,000 to 10,000 in number and each circular with the diameter of the nozzles being 50 to 200 μm.

12. The microorganism collecting device of claim 10 wherein the collection plate is formed from a solid medium whose primary materials include glass, quartz, resin (polypropylene, polyethylene terephthalate, polycarbonate, polystyrene, acrylonitrile-butadiene-styrene resin, polymethacrylic acid methyl ester or other acrylic resin, polydimethylsiloxane), metal (pure metals such as iron, aluminum, copper, tin, gold, silver, and the like and alloys such as alloy steel, copper alloy, aluminum alloy, nickel alloy, and the like), gelatin, and agar.

13. The microorganism collecting device of claim 9 wherein the collection plate includes concentric ring structures of different sizes whose top surfaces act as capture surfaces of the collection plate, and wherein the spaces between the concentric ring structures act as air vents.

14. A method for collecting airborne microorganisms that involves the use of the microorganism collecting device of claim 9, the method comprising the steps of:
  causing the air to flow through the nozzles of the perforated plate toward the capture surface(s) of the collection plate;
  causing the capture surface(s) to capture the microorganisms contained in the air; and
  causing the air to flow toward both the air vent and the second air vent after flowing past the nozzles.

\* \* \* \* \*